US009066769B2

(12) United States Patent
Truckai et al.

(10) Patent No.: US 9,066,769 B2
(45) Date of Patent: Jun. 30, 2015

(54) BONE TREATMENT SYSTEMS AND METHODS

(75) Inventors: Csaba Truckai, Saratoga, CA (US);
Robert Luzzi, Pleasanton, CA (US);
Andrew Kohm, San Mateo, CA (US);
John H. Shadduck, Tiburon, CA (US)

(73) Assignee: DFINE, Inc., San Jose, CA (US)

( * ) Notice: Subject to any disclaimer, the term of this patent is extended or adjusted under 35 U.S.C. 154(b) by 1269 days.

(21) Appl. No.: 12/345,937

(22) Filed: Dec. 30, 2008

(65) Prior Publication Data

US 2009/0198242 A1 Aug. 6, 2009

Related U.S. Application Data

(60) Provisional application No. 61/009,699, filed on Dec. 31, 2007, provisional application No. 61/009,659, filed on Dec. 31, 2007, provisional application No. 61/009,671, filed on Dec. 31, 2007, provisional application No. 61/009,673, filed on Dec. 31, 2007.

(51) Int. Cl.
*A61B 17/88* (2006.01)
*A61B 17/00* (2006.01)
*A61B 19/00* (2006.01)

(52) U.S. Cl.
CPC ......... *A61B 17/8822* (2013.01); *A61B 17/8816* (2013.01); *A61B 17/8836* (2013.01); *A61B 2017/8844* (2013.01); *A61B 2017/00022* (2013.01); *A61B 2017/00411* (2013.01); *A61B 2017/00955* (2013.01); *A61B 2019/464* (2013.01)

(58) Field of Classification Search
CPC ........... A61B 17/7094; A61B 17/7097; A61B 17/8802–17/8847; A61B 2017/8813–2017/8844
USPC ...................................................... 606/92–95
See application file for complete search history.

(56) References Cited

U.S. PATENT DOCUMENTS

| | | | |
|---|---|---|---|
| 2006/0089655 A1* | 4/2006 | Watkins et al. | 606/92 |
| 2006/0122623 A1* | 6/2006 | Truckai et al. | 606/94 |
| 2006/0122624 A1* | 6/2006 | Truckai et al. | 606/94 |
| 2006/0122625 A1* | 6/2006 | Truckai et al. | 606/94 |
| 2007/0027230 A1 | 2/2007 | Beyar et al. | |

* cited by examiner

*Primary Examiner* — Michael T Schaper
(74) *Attorney, Agent, or Firm* — Knobbe, Martens, Olson & Bear, LLP

(57) ABSTRACT

Systems and methods for treating vertebral compression fractures are discussed. In an embodiment, a method includes mixing bone cement precursors thereby causing a first chemical curing reaction characterized by a first time-viscosity profile, controllably applying energy to the bone cement from an external source to modify the first time-viscosity profile to a second time-viscosity profile, and injecting the cement into bone at a substantially constant viscosity greater than about 1000 Pa·s to greater than about 5000 Pa·s over an extended working time. In another embodiment, a bone cement injector system is provided that includes a first handle component that is detachably coupled to a second sleeve component having a distal end for positioning in bone and a flow channel extending through the first and second components. The system includes first and second thermal energy emitters for delivering energy to bone cement flows in a flow channel portion in the first and second components, respectively.

20 Claims, 13 Drawing Sheets

BONE TREATMENT SYSTEMS AND METHODS

CROSS-REFERENCE TO RELATED APPLICATIONS

This application claims the benefit of priority under 35 U.S.C. §119(e) of U.S. Provisional Application No. 61/009,699, filed on Dec. 31, 2007, entitled Bone Treatment Systems And Methods; No. 61/009,659, filed on Dec. 31, 2007, entitled Bone Treatment Systems And Methods; No. 61/009,671, filed on Dec. 31, 2007, entitled Bone Treatment Systems And Methods; and No. 61/009,673, filed on Dec. 31, 2007, entitled Bone Treatment Systems And Methods, the entirety of which are hereby incorporated by reference and should be considered a part of this specification.

This application is further related to the following U.S. patent application Ser. No. 11/209,035 filed Aug. 22, 2005, titled Bone Treatment Systems and Methods; Provisional Application No. 60/842,805filed Sep. 7, 2006 titled Bone Treatment Systems and Methods; No. 60/713,521filed Sep. 1, 2005 titled Bone Treatment Systems and Methods; No. 60/929,936filed Apr. 30, 2007 titled Bone Treatment Systems and Methods and No. 60/899,487filed Feb. 5, 2007 titled Bone Treatment Systems and Methods. The entire contents of all of the above applications are hereby incorporated by reference and should be considered a part of this specification.

BACKGROUND

1. Field of the Invention

Embodiments of the present disclosure relate to bone cement injection systems, and, in certain embodiments, provide systems and methods for on-demand control of bone cement viscosity for treating vertebral compression fractures and for preventing cement extravasation.

2. Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at about 26%. The prevalence increases with age, reaching approximately 40% among 80-year-old women. Medical advances aimed at slowing or arresting bone loss from aging have not provided solutions to this problem. Further, the population affected will grow steadily as life expectancy increases. Osteoporosis affects the entire skeleton but most commonly causes fractures in the spine and hip. Spinal or vertebral fractures also cause other serious side effects, with patients suffering from loss of height, deformity and persistent pain which can significantly impair mobility and quality of life. Fracture pain usually lasts 4 to 6 weeks, with intense pain at the fracture site. Chronic pain often occurs when one vertebral level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, with collagen, calcium salts, and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporosis bone, the sponge-like cancellous bone has pores or voids that increase in dimension making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. Vertebroplasty is the percutaneous injection of PMMA (polymethyl methacrylate) into a fractured vertebral body via a trocar and cannula. The targeted vertebra is identified under fluoroscopy. A needle is introduced into the vertebral body under fluoroscopic control, to allow direct visualization. A bilateral transpedicular (through the pedicle of the vertebra) approach is typical but the procedure can be done unilaterally. The bilateral transpedicular approach allows for more uniform PMMA infill of the vertebra.

In a bilateral approach, approximately 1 to 4 ml of PMMA is used on each side of the vertebra. Since the PMMA needs to be forced into the cancellous bone, the techniques require high pressures and fairly low viscosity cement. Since the cortical bone of the targeted vertebra may have a recent fracture, there is also the potential for PMMA leakage. The PMMA cement contains radiopaque materials so that, when injected under live fluoroscopy, cement localization and leakage can be observed. The visualization of PMMA injection and extravasation are critical to the technique, enabling the physician to terminate PMMA injection when leakage is evident. The cement is injected using syringes to allow the physician manual control of injection pressure.

Kyphoplasty is a modification of percutaneous vertebroplasty. Kyphoplasty involves a preliminary step including the percutaneous placement of an inflatable balloon tamp in the vertebral body. Inflation of the balloon creates a cavity in the bone prior to cement injection. The proponents of percutaneous kyphoplasty have suggested that high pressure balloon-tamp inflation can at least partially restore vertebral body height. In kyphoplasty, some physicians state that PMMA can be injected at a lower pressure into the collapsed vertebra since a cavity exists, when compared to conventional vertebroplasty.

The principal indications for any form of vertebroplasty are osteoporotic vertebral collapse with debilitating pain. Radiography and computed tomography are performed in the days preceding treatment to determine the extent of vertebral collapse, the presence of epidural or foraminal stenosis caused by bone fragment retropulsion, the presence of cortical destruction or fracture and the visibility and degree of involvement of the pedicles.

Leakage of PMMA during vertebroplasty can result in very serious complications, including compression of adjacent structures that may necessitate emergency decompressive surgery. See "Anatomical and Pathological Considerations in Percutaneous Vertebroplasty and Kyphoplasty: A Reappraisal of the Vertebral Venous System", Groen, R. et al, Spine Vol. 29, No. 13, pp 1465-1471 2004. Leakage or extravasation of PMMA is a critical issue and can be divided into paravertebral leakage, venous infiltration, epidural leakage, and intradiscal leakage. The exothermic reaction of PMMA carries potential catastrophic consequences if thermal damage extends to the dural sac, cord, and nerve roots. Surgical evacuation of leaked cement in the spinal canal has been reported. It has been found that leakage of PMMA is related to various clinical factors such as the vertebral compression pattern, the extent of the cortical fracture, bone mineral density, the interval from injury to operation, the amount of PMMA injected, and the location of the injector tip. In one recent study, close to 50% of vertebroplasty cases resulted in leakage of PMMA from the vertebral bodies. See Hyun-Woo Do et al, "The Analysis of Polymethylmethacrylate Leakage after Vertebroplasty for Vertebral Body Compression Fractures", *J. of Korean Neurosurg. Soc.* Vol. 35, No. 5 (5/2004) pp. 478-82.

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol. 2004 February; 25(2):175-80. The study found that about 58% of vertebral bodies adjacent to a disc with cement leakage fractured during the follow-up period compared with about 12% of vertebral bodies adjacent to a disc without cement leakage.

Another life-threatening complication of vertebroplasty is pulmonary embolism. See Bernhard, J. et al, "Asymptomatic diffuse pulmonary embolism caused by acrylic cement: an unusual complication of percutaneous vertebroplasty", Ann. Rheum. Dis. 2003; 62:85-86. The vapors from PMMA preparation and injection also are cause for concern. See Kirby, B, et al., "Acute bronchospasm due to exposure to polymethylmethacrylate vapors during percutaneous vertebroplasty", Am. J. Roentgenol. 2003; 180:543-544.

In both higher pressure cement injection (vertebroplasty) and balloon-tamped cementing procedures (kyphoplasty), the methods do not provide for well controlled augmentation of vertebral body height. The direct injection of bone cement simply follows the path of least resistance within the fractured bone. The expansion of a balloon applies also compacting forces along lines of least resistance in the collapsed cancellous bone. Thus, the reduction of a vertebral compression fracture is not optimized or controlled in high pressure balloons as forces of balloon expansion occur in multiple directions.

In a kyphoplasty procedure, the physician often uses very high pressures (e.g., up to about 200 or 300 psi) to inflate the balloon, which may crush and compact cancellous bone. Expansion of the balloon under high pressures close to cortical bone can also fracture the cortical bone, typically the endplates, which can cause regional damage to the cortical bone with the risk of cortical bone necrosis. Such cortical bone damage is highly undesirable as the endplate and adjacent structures provide nutrients for the disc.

Kyphoplasty also does not provide a distraction mechanism capable of 100% vertebral height restoration. Further, the kyphoplasty balloons under very high pressure typically apply forces to vertebral endplates within a central region of the cortical bone that may be weak, rather than distributing forces over the endplate.

SUMMARY OF THE INVENTION

Certain embodiments of the invention provide bone cement injectors and control systems that allow for vertebroplasty procedures that inject cement having a substantially constant viscosity over an extended cement injection interval. A computer controller is provided to control cement flow parameters in the injector and energy delivery parameters for selectively accelerating polymerization of bone cement before the cement contacts the patient's body.

In accordance with one embodiment, a bone treatment system is provided. The system comprises a bone fill material injector system comprising an injector configured to be at least partially introduced into a bone. The system also comprises a thermal energy emitter operatively coupled to the injector system and configured for delivering energy to a flow of bone fill material through the injector system. An electronic controller is configured to modulate the delivery of energy from the thermal energy emitter to the flow of bone fill material based at least in part on a sensed pressure in the injector system to achieve a desired bone fill material viscosity.

In accordance with another embodiment, a method for treating bone is provided. The method comprises flowing bone fill material through a bone fill material injector system having at least a portion of an injector positioned in a cancellous bone portion of the bone, delivering energy to the flow of bone fill material via a thermal energy emitter in communication with the bone fill material injector system, and electronically controlling the delivery of energy to the thermal energy emitter to achieve a desired bone fill material viscosity based at least in part on a sensed pressure in the bone fill material injector system.

In accordance with still another embodiment, a bone treatment system is provided. The system comprises a handle component in communication with one or more energy sources, and a sleeve component having a proximal portion attached to the handle component and a distal end configured for positioning in a bone, the handle and sleeve components defining a flow channel extending therethrough. The system also comprises a first energy emitter configured for delivering energy to a bone fill material flow in a flow channel portion in the handle component, and a second energy emitter configured for delivering energy to a bone fill material flow in a flow channel portion in the sleeve component.

In accordance with yet another embodiment, a method for treating a bone is provided. The method comprises inserting at least a portion of an injector of a bone cement injector system within a vertebral body, providing a flow of a settable bone cement having a first viscosity into a proximal portion of the injector, and applying energy to the bone cement via a thermal energy emitter of the bone cement injector system to cause the viscosity of the bone cement to change from the first viscosity to a second viscosity, different than the first viscosity. The method also comprises urging the bone cement having the second viscosity from the proximal portion toward the distal portion of the injector, applying energy to the bone cement via another thermal energy emitter of the bone cement injector system disposed within the injector to cause the flow of bone cement exiting an outlet of the injector to achieve a third viscosity, different than the first and second viscosities, and introducing the bone cement with said third viscosity into cancellous bone.

These and other objects of the present invention will become readily apparent upon further review of the following drawings and specification.

BRIEF DESCRIPTION OF THE DRAWINGS

In order to better understand embodiments of the present disclosure and to see how they may be carried out in practice, selected embodiments are next described, by way of non-limiting examples only, with reference to the accompanying drawings, in which like reference characters denote corresponding features consistently throughout similar embodiments in the attached drawings.

DETAILED DESCRIPTION OF THE PREFERRED EMBODIMENTS

Figure 1:
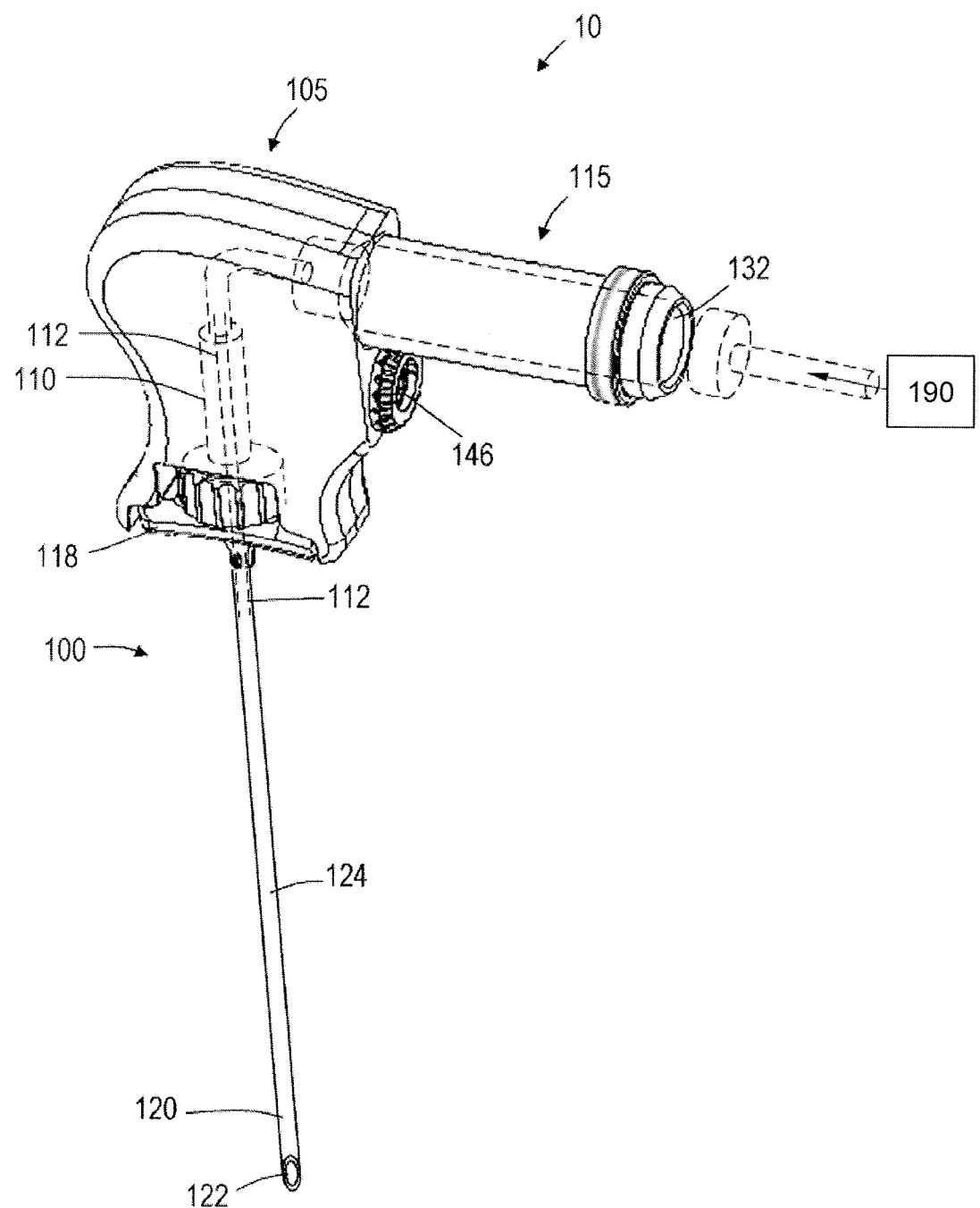
FIG. 1 is a perspective view of a bone cement injection system in accordance with one embodiment of the present disclosure.

Reference will now be made to the embodiments illustrated in the drawings and accompanying text. As background, a vertebroplasty procedure using embodiments of the present disclosure would introduce the injector of FIGS. 1-2 through a pedicle of a vertebra, or in a parapedicular approach, for accessing the osteoporotic cancellous bone. The initial aspects of the procedure are similar to a conventional percutaneous vertebroplasty where the patient is placed in a prone position on an operating table. The patient is typically under conscious sedation, although general anesthesia is an alternative. The physician injects a local anesthetic (e.g., 1% Lidocaine) into the region overlying the targeted pedicle or pedicles as well as the periosteum of the pedicle(s). Thereafter, the physician uses a scalpel to make a 1 to 5 mm skin incision over each targeted pedicle. Thereafter, the bone cement injector is advanced through the pedicle into the anterior region of the vertebral body, which typically is the region of greatest compression and fracture. The physician confirms the introducer path posterior to the pedicle, through the pedicle and within the vertebral body by anteroposterior and lateral X-Ray projection fluoroscopic views. The introduction of infill material, as described below, can be imaged several times, or continuously, during the treatment depending on the imaging method.

The terms "bone cement, bone fill or fill material, infill material or composition" includes its ordinary meaning as known to those skilled in the art and may include any material for infilling a bone that includes an in-situ hardenable or settable cement, or a composition that can be infused with such a hardenable cement. The fill material also can include other "fillers" including, but not limited to, filaments, microspheres, powders, granular elements, flakes, chips, tubules and the like, autograft or allograft materials, as well as other chemicals, pharmacological agents or other bioactive agents.

The term "flowable material" includes its ordinary meaning as known to those skilled in the art and may include a material continuum that is unable to withstand a static shear stress and responds with an irrecoverable flow (e.g., a fluid), unlike an elastic material or elastomer that responds to shear stress with a recoverable deformation. Flowable material includes fill materials or composites that include a first component (e.g., a fluid) and a second component that may include an elastic or inelastic material component that responds to stress with a flow, no matter the proportions of the first and second component, and where the above shear test does not apply to the second component alone.

The terms "substantially" or "substantial" mean largely but not entirely. For example, substantially may mean about 50% to about 99.999%, about 80% to about 99.999% or about 90% to about 99.999%.

The term "vertebroplasty" includes its ordinary meaning as known to those skilled in the art and may include any procedure wherein fill material is delivered into the interior of a vertebra.

The term "cancellous bone", also known as "spongy bone" includes its ordinary meaning as known to those skilled in the art and may include a porous bone having a honeycombed or spongy appearance that encloses naturally occurring, pre-existing spaces filled with bone marrow, the honeycomb-like structure organized into a three-dimensional matrix or lattice of bony processes, called trabeculae, arranged along lines of stress.

The term "cortical bone", also known as "compact bone" includes its ordinary meaning as known to those skilled in the art and includes the dense outer surface of bones that forms a protective layer around the internal bone including cancellous bone.

The term "osteoplasty" includes its ordinary meaning as known to those skilled in the art and may include any procedure wherein fill material is delivered into the interior of a bone.

Figure 2:
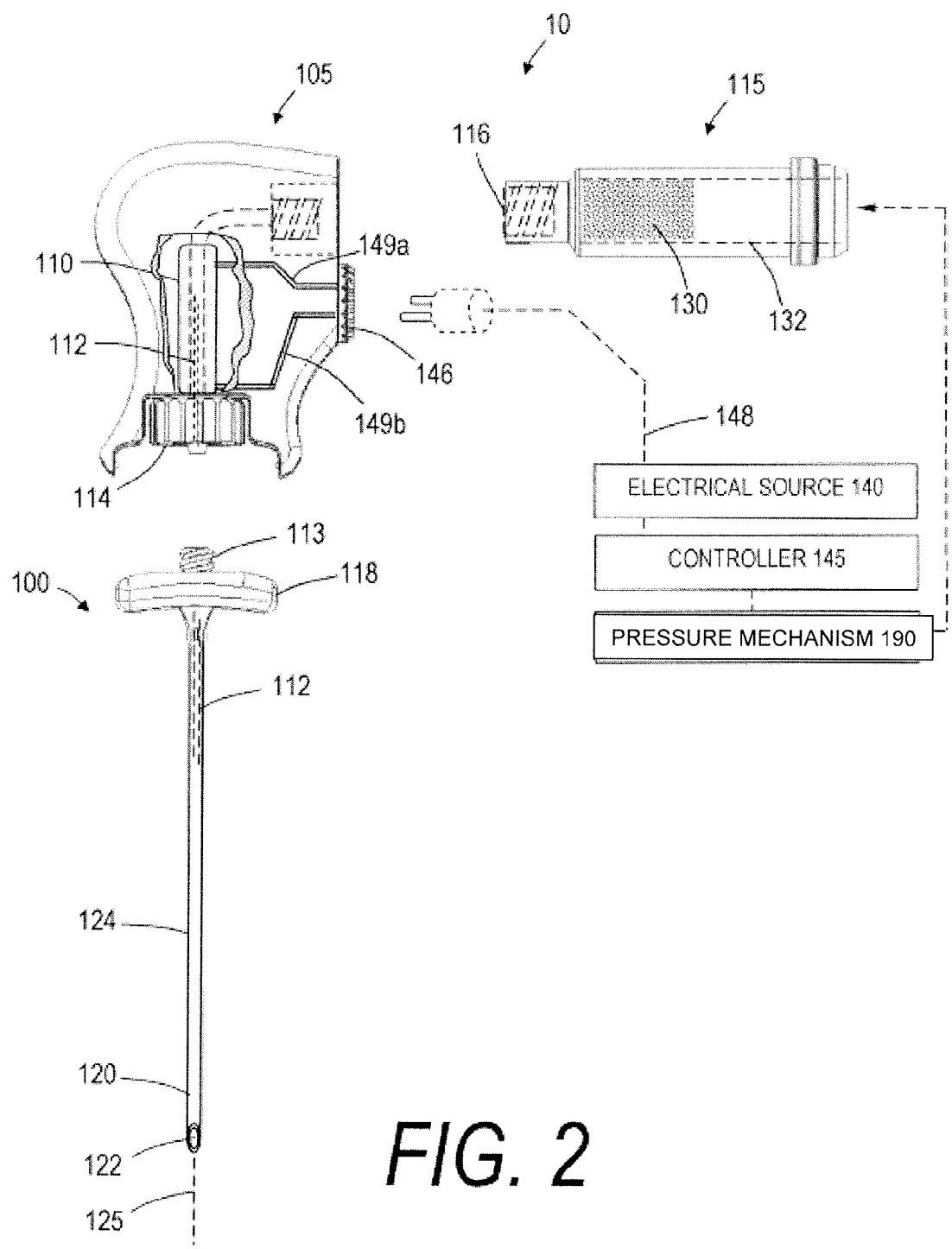
FIG. 2 is another view of the system of FIG. 1 with the bone cement injection components de-mated from one another.

In FIG. 1, a system 10 is shown that includes a first component, or bone cement injector, 100 a distal end 120 of which can extend into the cancellous bone portion of a vertebra, and a second component, or cement activation component, 105 which includes an emitter 110 for applying energy to bone cement. The first and second components 100 and 105 include a flow passageway, or channel, 112 extending therethrough for delivering a flowable bone cement into a bone. In certain embodiments, the bone cement injector component 100 and the cement activation component 105 can be integrated into a unitary device (e.g., a single piece). In other embodiments, the bone cement injector component 100 and the cement activation component 105 can be de-mateable, as shown in FIG. 2, by a coupling mechanism such as threaded portion 113 and rotatable screw-on fitting 114. As can be seen in FIGS. 1 and 2, a source of bone cement in the form of a syringe-type body 115 can also be coupled to the system by a coupling mechanism such as a threaded fitting 116.

Referring to FIG. 2, the bone cement injector 100 has proximal end 118 and distal end 120 with at least one flow outlet 122 to direct a flow of cement into a bone (e.g., a vertebra) so that the bone cement interdigitates with cancellous bone (e.g., flows through naturally-occurring pre-existing openings in cancellous bone). The extension portion 124 of the injector 100 may be a sleeve with flow passageway 112 extending therethrough to the flow outlet 122. In an embodiment, the flow outlet 122 can include a side port that directs cement flow transversely relative to the axis 125 of extension portion 124. In another embodiment, the flow outlet 122 can be positioned at about the distal termination of extension portion 124 in order to direct cement flows distally. In another embodiment (not shown) the extension portion 124 can include first and second concentric sleeves having first and second flow outlets, respectively, that can be rotated relative to one another in order to align or misalign the first and second flow outlets to allow selectively directed cements flow to be more or less axial relative to axis 125 of extension portion 124. The extension portion may further be constructed of any suitable metal or plastic.

Now turning to the cut-away view of FIG. 2, it can be seen that the second component 105 can include a handle portion that carries an emitter 110 for applying thermal energy to a cement flow within flow channel 112 that extends through the emitter 110. As will be described further below, the emitter 110 can be operated to apply thermal energy to bone cement 130 delivered from chamber 132 of source 115 to flow through the emitter 110 to therein to provide "on-demand" a selected higher viscosity cement as the cement exits the injector flow outlet 122 into bone. The controlled application of energy to bone cement 130 allows the physician to advantageously select a setting rate for the cement to reach a selected polymerization endpoint as the cement is being introduced into the vertebra, thus allowing a high viscosity that will be prevent unwanted cement extravasation.

Figure 3:
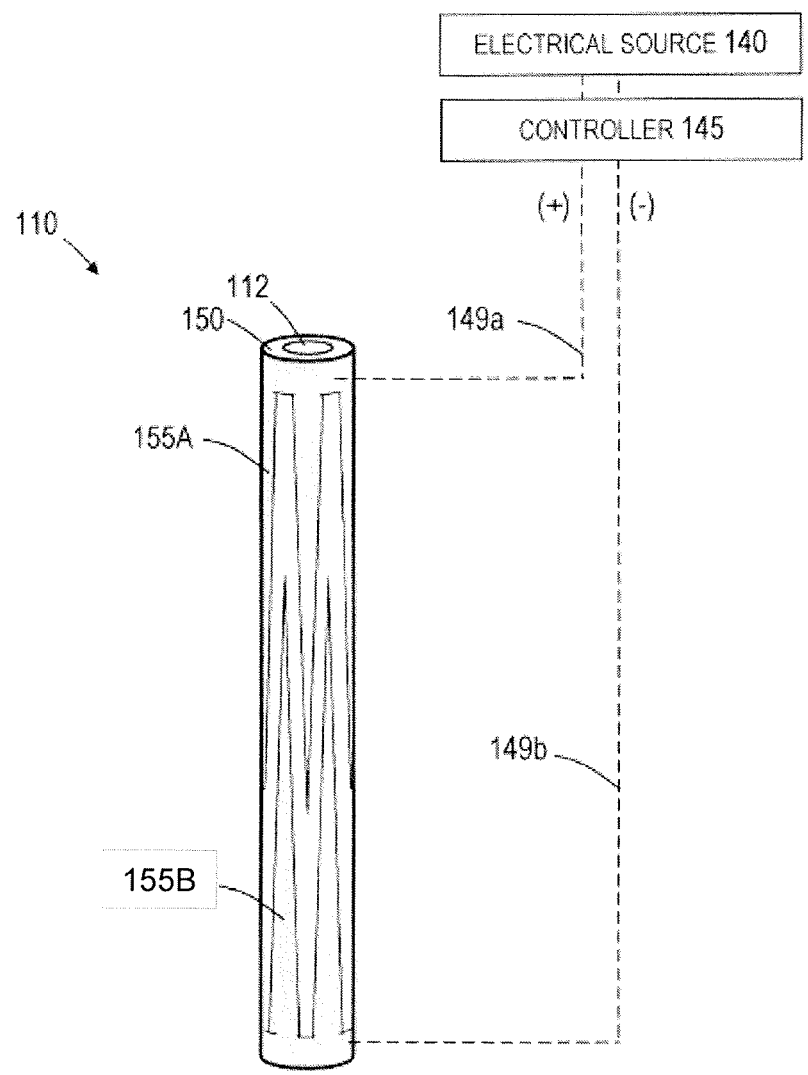
FIG. 3 is an embodiment of a thermal emitter component of the system of FIGS. 1 and 2.

Referring to FIGS. 2 and 3, in one embodiment, the thermal energy emitter 110 is coupled to electrical source 140 and controller 145 by a electrical connector 146 and cable 148. In FIG. 2, it can be seen that electrical leads 149a and 149b couple with connector 146 and extend and electrically connect to the emitter 110. As can be seen in FIG. 3, one embodiment of thermal energy emitter 110 has a wall portion 150 that comprises a polymeric positive temperature coefficient of resistance (PTCR) material with spaced apart interlaced surface electrodes 155A and 155B as described in co-pending Provisional Application No. 60/907,468 filed Apr. 3, 2007 titled Bone Treatment Systems and Methods. In this embodiment, the thermal emitter 110 and wall 150 thereof will resistively heat to thereby cause controlled thermal effects in bone cement 130 flowing therethrough. It should be appreciated that FIG. 3 is a schematic representation of one embodiment of thermal energy emitter 110 which can have any elongated or truncated shape or geometry, tapered or non-tapered form, or comprise the wall of a collapsible thin-wall element. Further, the positive (+) and negative (−) polarity electrodes 155A and 155B can have any spaced apart arrangement, for example radially spaced apart, helically spaced apart, axially spaced apart or any combination thereof. This resistively heated PTCR material of the emitter 110 may further generate a signal that indicates flow rate as described in Provisional Application No. 60/907,468, which in turn can be utilized by controller 145 to modulate energy applied to the bone cement therein, and/or modulate the flow rate of cement 130 which can be driven by a motor or stored energy mechanism. In another embodiment, the emitter can be any non-PTCR resistive heater such as a resistive coil heater. However, the emitter 110 can have other suitable configurations.

In other embodiments, the thermal energy emitter 110 can be a PTCR constant temperature heater as described above or selected from the group of emitters consisting of at least one of a resistive heater, a fiber optic emitter, a light channel, an ultrasound transducer, an electrode and an antenna. Accordingly in any such embodiment, the energy source 140 can comprise at least one of a voltage source, a radiofrequency source, an electromagnetic energy source, a non-coherent light source, a laser source, an LED source, a microwave source, a magnetic source and an ultrasound source that is operatively coupled to the emitter 110.

Referring FIG. 2, it can be understood that a pressure source or pressure mechanism 190 is coupleable to the bone cement source or syringe 115 for driving the bone cement 130 through the system 10. The pressure source 190 can be any suitable manual drive system or an automated electrically driven system such as any pump (e.g., motor driven pump), screw drive, pneumatic drive, hydraulic drive, cable drive or the like. Such automated drive systems can be coupled to the controller 145 to modulate the flow rate or pressure of cement through the system.

Figure 4:
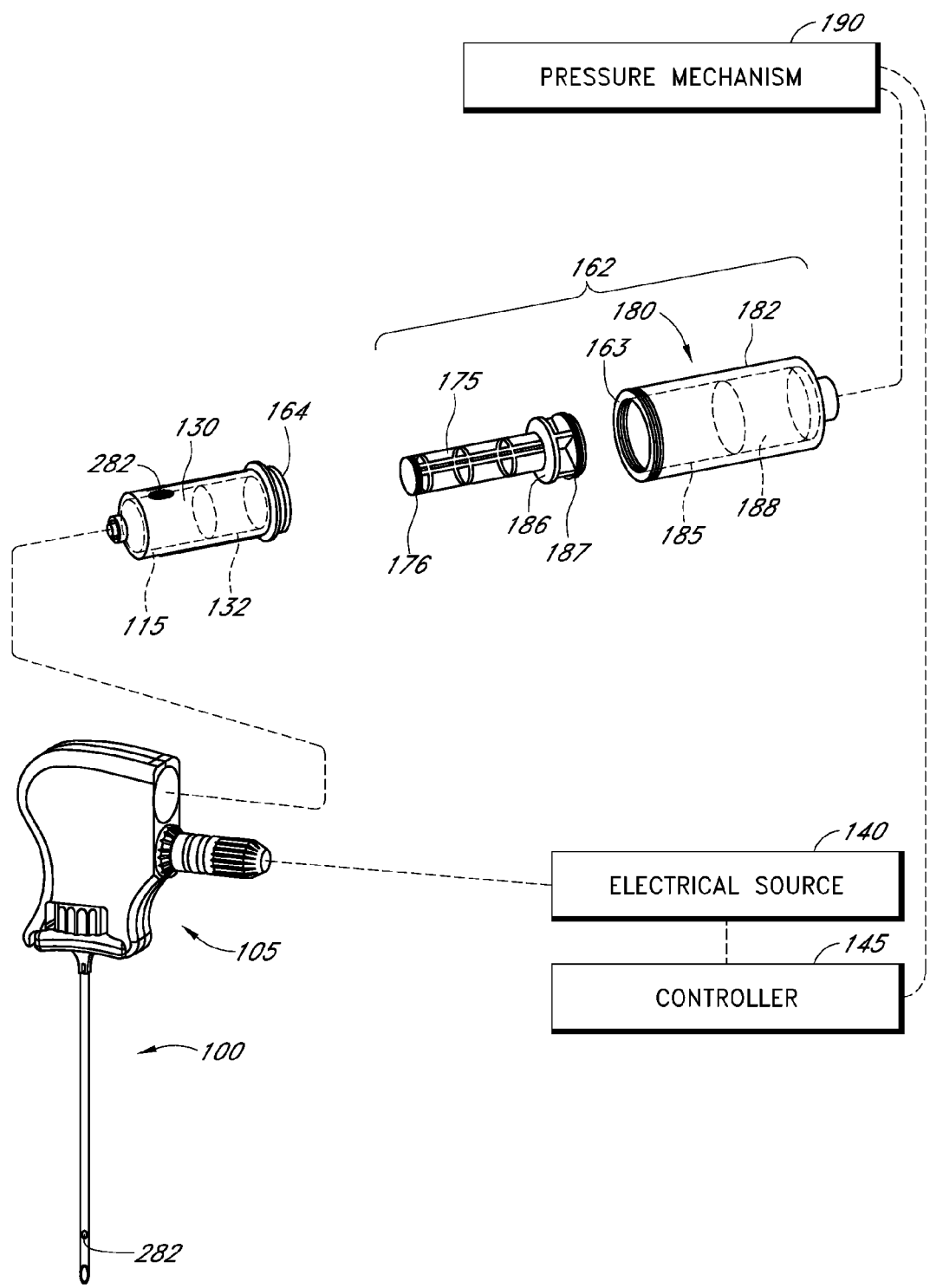
FIG. 4 is another view of the components of the system of FIGS. 1-2 together with an embodiment of a pressurization mechanism and block diagram of an embodiment of an energy source and controller.
Figure 5:
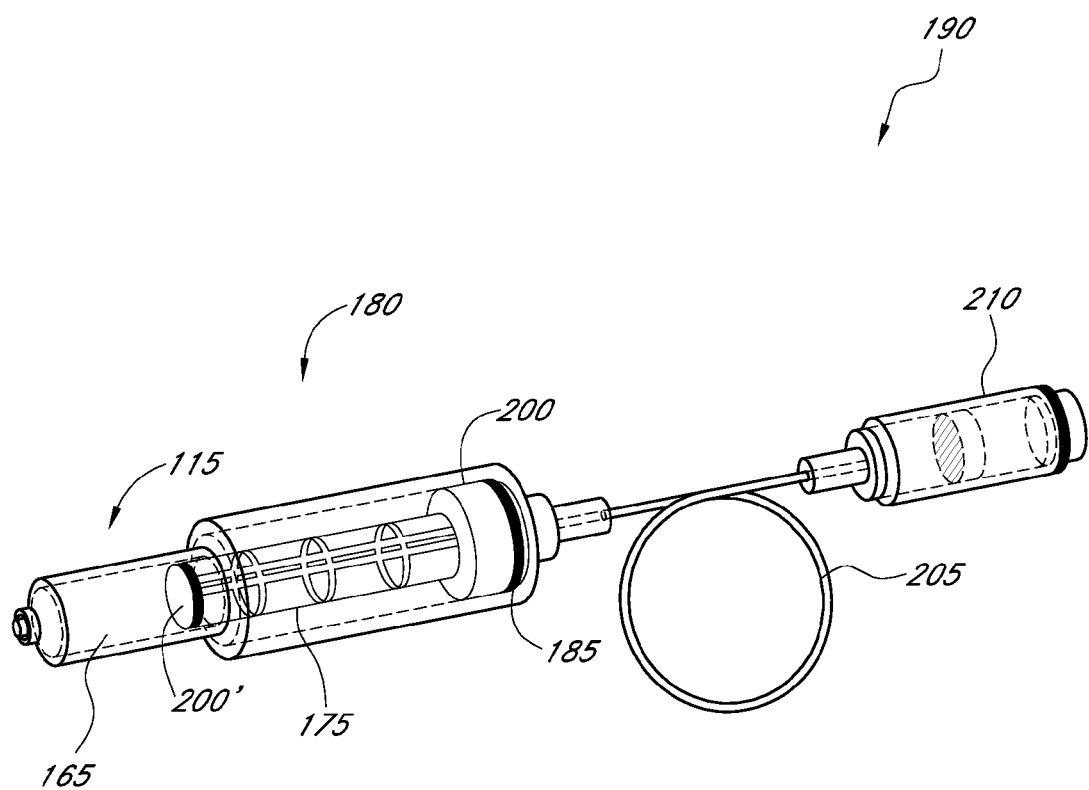
FIG. 5 is an enlarged, assembled view of several components of the system of FIG. 4.
Figure 6:
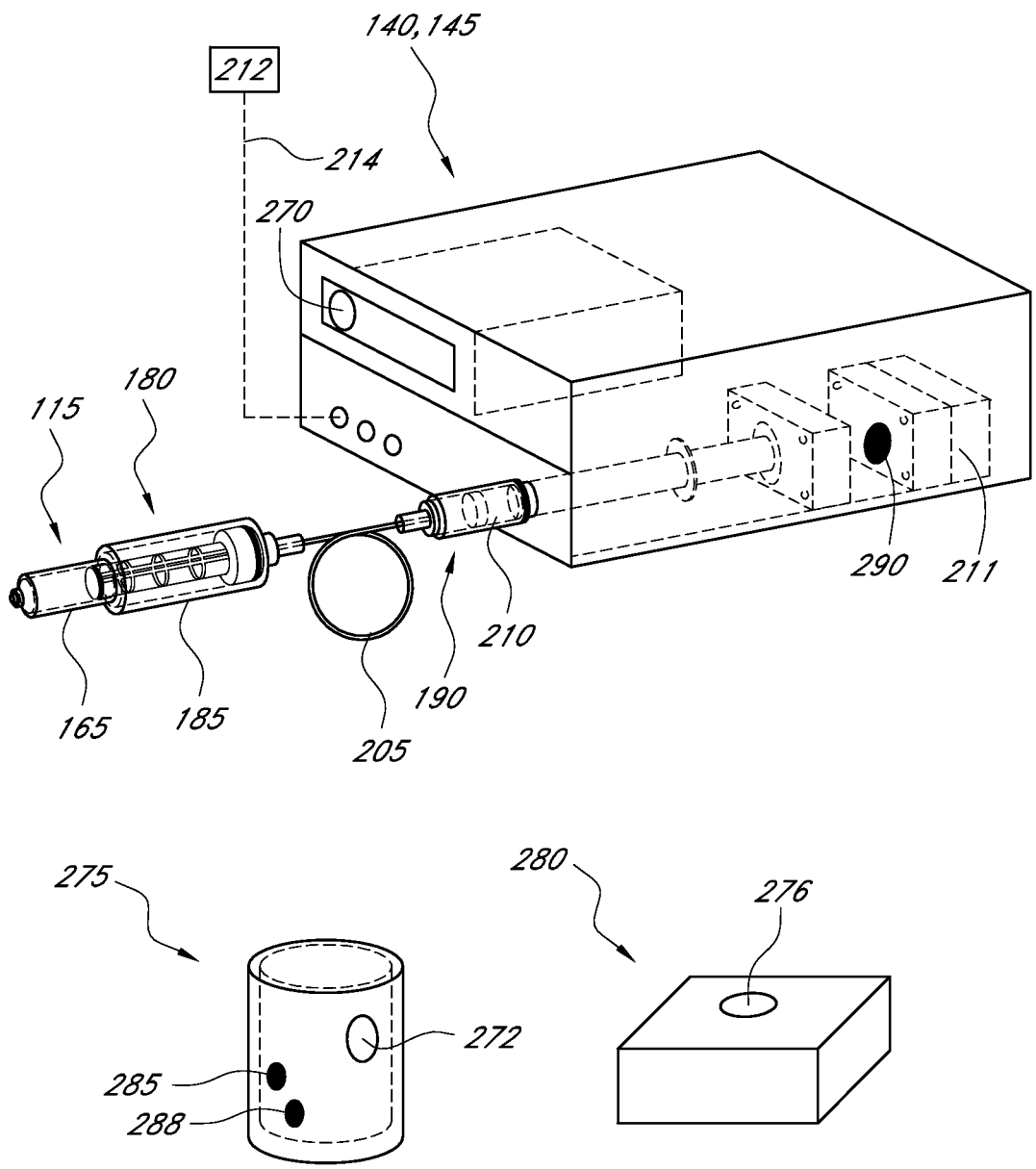
FIG. 6 is a perspective view of components of the system of FIGS. 1-5 with a perspective view of one embodiment of an energy source and controller.

In one embodiment shown in FIGS. 4-6, the pressure source 190 includes a hydraulic system 162 with a fitting 163 that may detachably couple to a fitting 164 of the bone cement source 115. In this embodiment, the bone cement source 115 includes a syringe body with cement-carrying bore or chamber 132 that carries a pre-polymerized, partially polymerized or recently-mixed bone cement 130 therein. The hydraulic system 162 can further include a rigid plunger or actuator member 175 with o-ring or rubber head 176 that can move in chamber 132 to push the cement 130 through the syringe chamber 132 and the flow channel 112 in the system 100.

Still referring to FIGS. 4-6, a force application and amplification component 180 of the hydraulic system 162 can be de-mateably coupled to the bone cement source 115, where the component 180 includes a body 182 with a pressurizable bore or chamber 185 that slidably receives the proximal end 186 of an actuator member 175. The proximal end 186 of the actuator member 175 includes an o-ring or gasket 187 so that the bore 185 can be pressurized with flow media 188 by the pressurizing mechanism 190 to drive the actuator member 175 distally to thereby displace bone cement 130 from chamber 132 in the cement source or syringe 115.

In one embodiment, the surface area of an interface 200 between the actuator member 175 and pressurized flow media 188 is substantially larger than the surface area of an interface 200' between the actuator member 175 and bone cement 130 to thereby provide pressure amplification between the pressurizable chamber 185 and chamber 132 of the cement source or syringe. In one embodiment as indicated in FIGS. 4 and 5, the surface area of interface 200 is at least 150% of the surface area of interface 200', at least 200% of the surface area of interface 200', at least 250% of the surface area of interface 200', and at least 300% of the surface area of interface 200'.

Referring to FIGS. 4 and 5, in one embodiment, a force amplification method of the present disclosure includes: (a) providing a bone fill material injector with a displaceable non-fluid actuator component intermediate a first fluid chamber and a second cement or fill-carrying chamber; (b) causing a flow of flow media at a first pressure into the first fluid chamber thereby displacing the actuator component to impinge on and eject bone cement or fill at a higher second pressure from the second chamber into a vertebra. The method provides a second pressure in the cement-carrying chamber 165 that is: at least 50% higher that the first pressure in the pressurizable chamber 185, at least 50% higher that the first pressure in the pressurizable chamber 185, at least 100% higher that the first pressure in the pressurizable chamber 185, at least 200% higher that the first pressure in the pressurizable chamber 185, at least 300% higher that the first pressure in the pressurizable chamber 185.

Referring to FIGS. 5 and 6, one embodiment of pressurizing system 190 includes a pneumatic or hydraulic line 205 that extends to pressurizing mechanism that can include a syringe pump 210 that is manually driven or motor-driven, (e.g., electrically driven), as is known in the art. In one embodiment as shown in FIG. 6, the syringe pump 210 is driven by an electric motor 211 operatively coupled to controller 145 to allow modulation of the pressure or driving force in combination with the control of energy delivery by the emitter 110 from the energy source 140. It should be appreciated that the pressurizing mechanism 210 can be any type of mechanism or pump known in the art to actuate the actuator member 175 to move the bone cement in chamber 165. For example, a suitable mechanism can be a piezoelectric element for pumping fluid, an ultrasonic pump element, a compressed air system for creating pressure, a compressed gas cartridge for creating pressure, an electromagnetic pump for creating pressure, an air-hammer system for creating pressure, a mechanism for capturing forces from a phase change in a fluid media, a spring mechanism for releaseably storing energy, a spring mechanism and a ratchet, a fluid flow system and a valve, a screw pump, a peristaltic pump, a diaphragm pump, or any rotodynamic pumps or any positive displacement pumps.

FIG. 6 also shows another feature of certain embodiments of the present disclosure, namely a remote switch 212 for actuating the pressurizing mechanism 190 as well as delivery of energy from the energy source 140 to the emitter 110. In one embodiment, a cable 214 extends from the controller 145 to the switch 212 so that the physician can advantageously stand outside or the radiation field created by any imaging system used while treating a vertebra or other bone treatment site. In another embodiment, the switch 212 can be wirelessly connected to the system as is known in the art. In another embodiment (not shown), the elongated cable 214 and switch 212 can be directly coupled to the injector or other components of the system.

In one embodiment, the bone treatment system includes a bone cement injector system including a thermal energy emitter 110 for delivering energy to the bone cement in the injector system, a controller 145 for modulating applied energy from the emitter to thereby control a curing reaction of the cement, and a sensor system operatively coupled to the injector system for measuring an operational parameter of bone cement within the system. In FIG. 6, in one embodiment, it can be seen that one sensor of the sensor system can include an ambient temperature sensor indicated at 270 which can be disposed in the controller assembly 140. The ambient temperature sensor 270 in the controller assembly 140 can allow for ambient temperature input into the system control algorithms for modulating applied energy from the emitter 110 based at least in part on ambient air temperature in the operating room environment, which can affect the time-viscosity curve of an exothermic PMMA bone cement.

In another embodiment, referring to FIG. 6, the system can include a temperature sensor 272 disposed in a mixing device or assembly 275 which can be any container that receives the bone cement precursors for mixing before placement of the mixed cement in the bone cement source 115 (see FIG. 6). It is useful to have a temperature sensor 272 in the cement mixing assembly because cement may be stored in a hospital in an environment having a lower or higher temperature than the operating room which also will affect the time-viscosity curve of the cement. The temperature sensor 272 can be operatively coupled to the controller by a cable or a wireless transmitter system. The sensor 272 can be unitary with the mixing assembly and disposable in one embodiment, or can be reusable and/or detachable from the mixing assembly 275 in another embodiment. In another embodiment, still referring to FIG. 6, a temperature sensor 276 can be operatively connected to one or more packages 280 of the bone cement precursors to thereby indicate the actual temperature of the cement precursor(s) prior to mixing, which will indicate the stored temperature and/or the length of time that such cement precursors have been in the operating room when compared to an ambient room temperature measured by sensor 270. In one embodiment, the sensor 276 can be a thermocouple or a thermochromic ink on the packaging that allows for visual identification of the temperature of the cement precursors for input of such temperature into the controller 145 to allow for automatic adjustment of the energy delivery algorithms of embodiments of the present disclosure based at least in part on the sensed temperature from the sensor 276. In another embodiment, referring back to FIG. 4, at least one temperature sensor 282 can be located in or on the cement source 115 of the system and/or in a distal portion of the injector component 100 for monitoring cement temperature in a cement flow within the system 10.

In another embodiment, the bone cement system and more particularly the cement mixing assembly 275 of FIG. 6 can include a sensor, switch, or indication mechanism 285 for indicating the time of initiation of bone cement mixing. Such a sensor or indication mechanism 285 can be any manually-actuated mechanism coupled to the controller or a mechanism that senses (e.g., automatically) the disposition of the cement precursors in the mixing assembly or the actuation of any moveable mixing component of the assembly. The system and controller 145 then can provide a visual, aural, or tactile signal indicating that a pre-determined mixing time interval has been reached, which will thus assure that a time zero post-mixing viscosity will be similar in all cases to thereby allow optimal applied energy as described above. The system also can include a sensor, switch, or indication mechanism 288 that indicates the termination of bone cement mixing, and thus time zero on a time-viscosity curve as discussed in detail with respect to FIG. 9, which is needed for setting the algorithms in the controller 145 for controlling applied energy and the cement flow rate.

In another embodiment, the bone cement system 10 includes a sensor that measures and indicates the bone cement flow rate within the flow passageway in the injector system. In the embodiment of FIG. 6, the motor drive system 211 may drive the cement via the hydraulic system at an approximately constant rate through the injector and emitter 110. For example, in one embodiment, a sensor 290 may be operatively coupled to the motor drive which can measure the force and/or pressure being applied by the drive to cause the desired cement flow through the system. This force measurement, in turn, may be used to sense any tendency for a slow-down in the desired flow rate, for example due to an unanticipated increase in viscosity of cement in the system. Upon sensing such an increase, the controller 145 can increase the flow rate (e.g., increase the drive pressure) or decrease the applied energy from emitter 110 to attain the desired cement viscosity and flow rate from the injector 100 into bone. Likewise, upon sensing a tendency for an increase in the desired flow rate, such as an unanticipated decrease in viscosity of the cement, the controller 145 can increase the flow rate (e.g., increase the drive pressure) or increase the applied energy from emitter 110 to ensure the desired cement viscosity and flow rate from the injector 100 into the bone is attained.

In further embodiments, one or more of the sensors 270, 272, 276, 282, 285, 288, 290 may be in communication with the controller 145 for input of data collected by the sensors into the controller 145. For example, in certain embodiments, an operator may obtain at least a portion of the data collected by the sensors 270, 272, 276, 282, 285, 288, 290 and manually input the relevant data into the controller 145. In alternative embodiments, one or more of the sensors 270, 272, 276, 282, 285, 288, 290 may possess a direct connection, such as a wired or wireless data connection with the controller 145, whereby the controller 145 may request data from the sensors 270, 272, 276, 282, 285, 288, 290 and/or the sensors 270, 272, 276, 282, 285, 288, 290 may communicate at least a portion of collected data to the controller 145.

Figure 7:
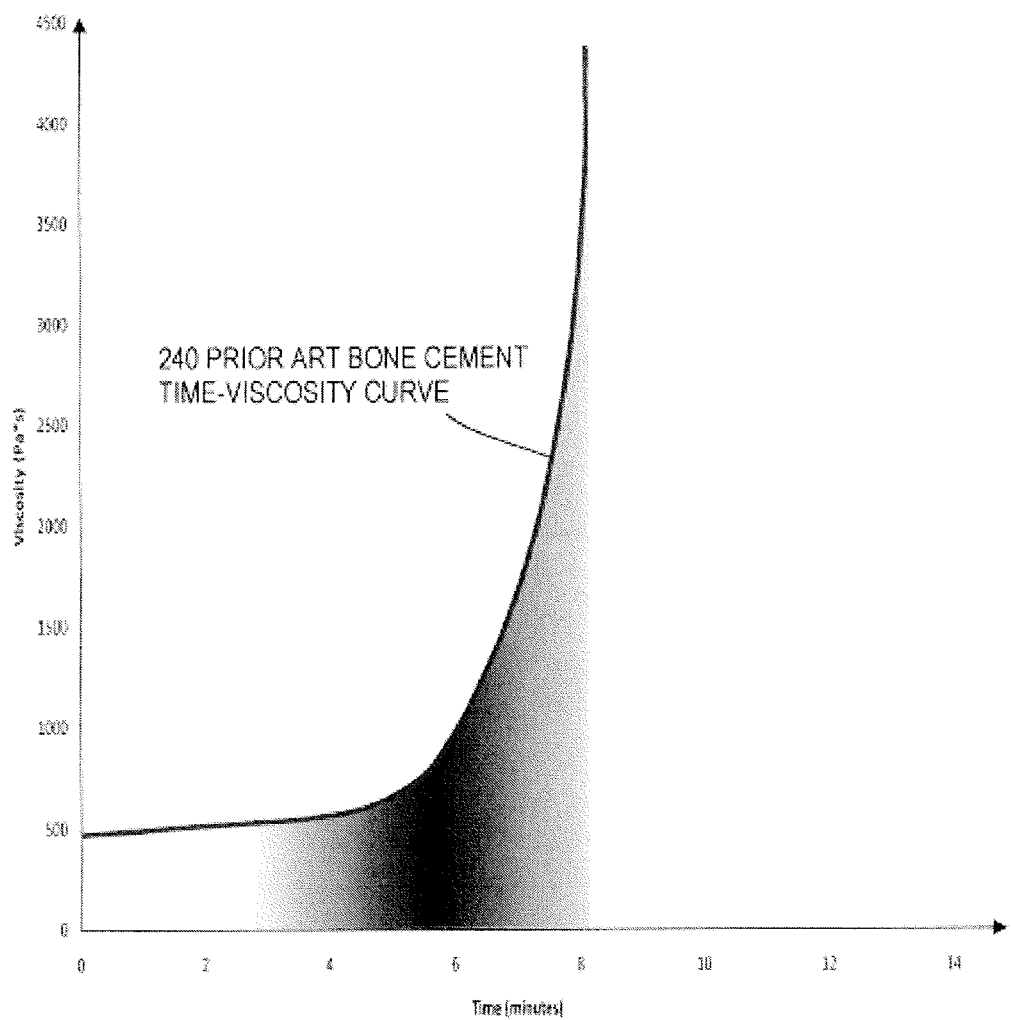
FIG. 7 is chart indicating a time-viscosity curve for a prior art PMMA bone cement.
Figure 8A:
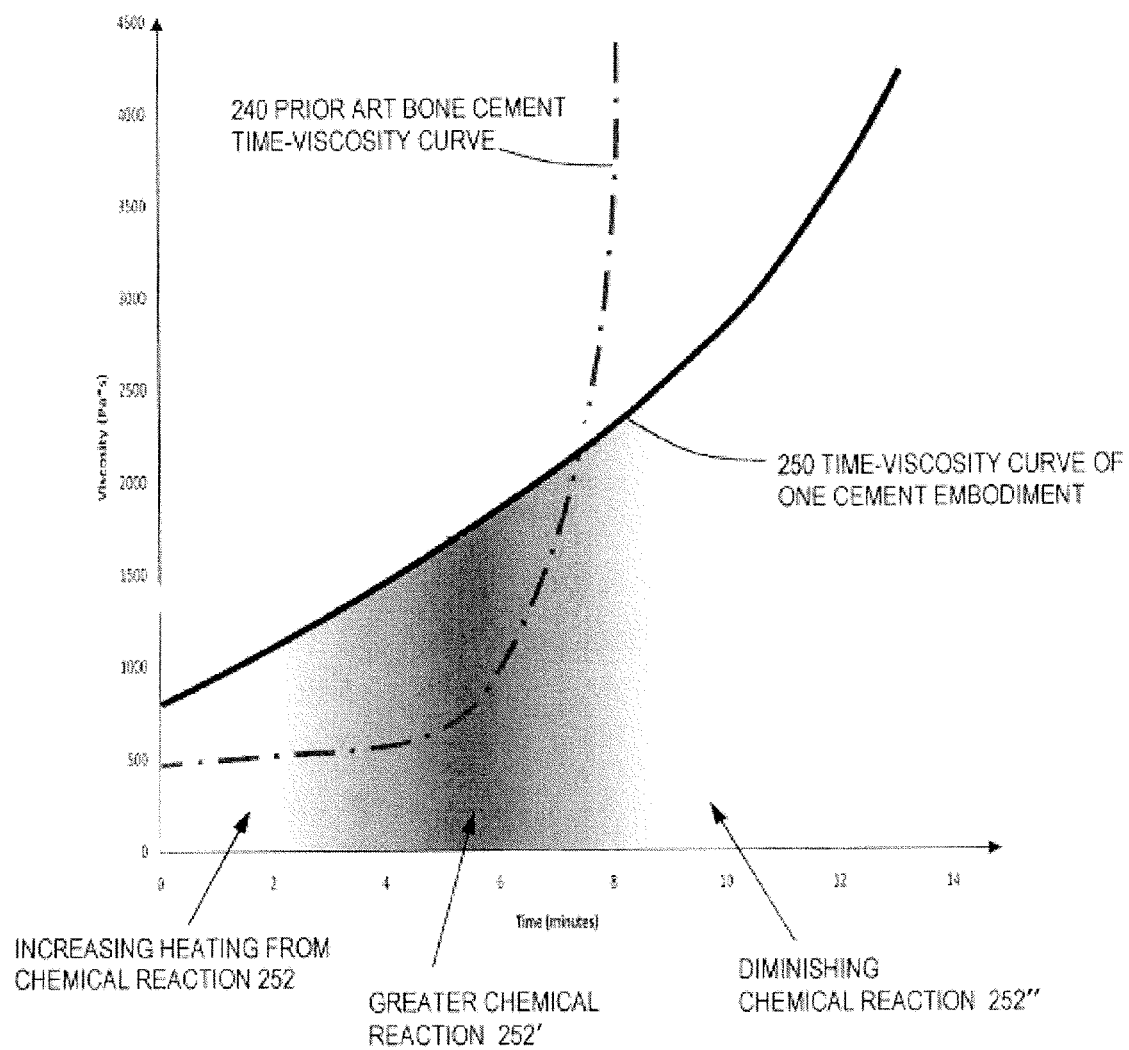
FIG. 8A is chart indicating a time-viscosity curve for an embodiment of a PMMA bone cement of the present disclosure.
Figure 8B:
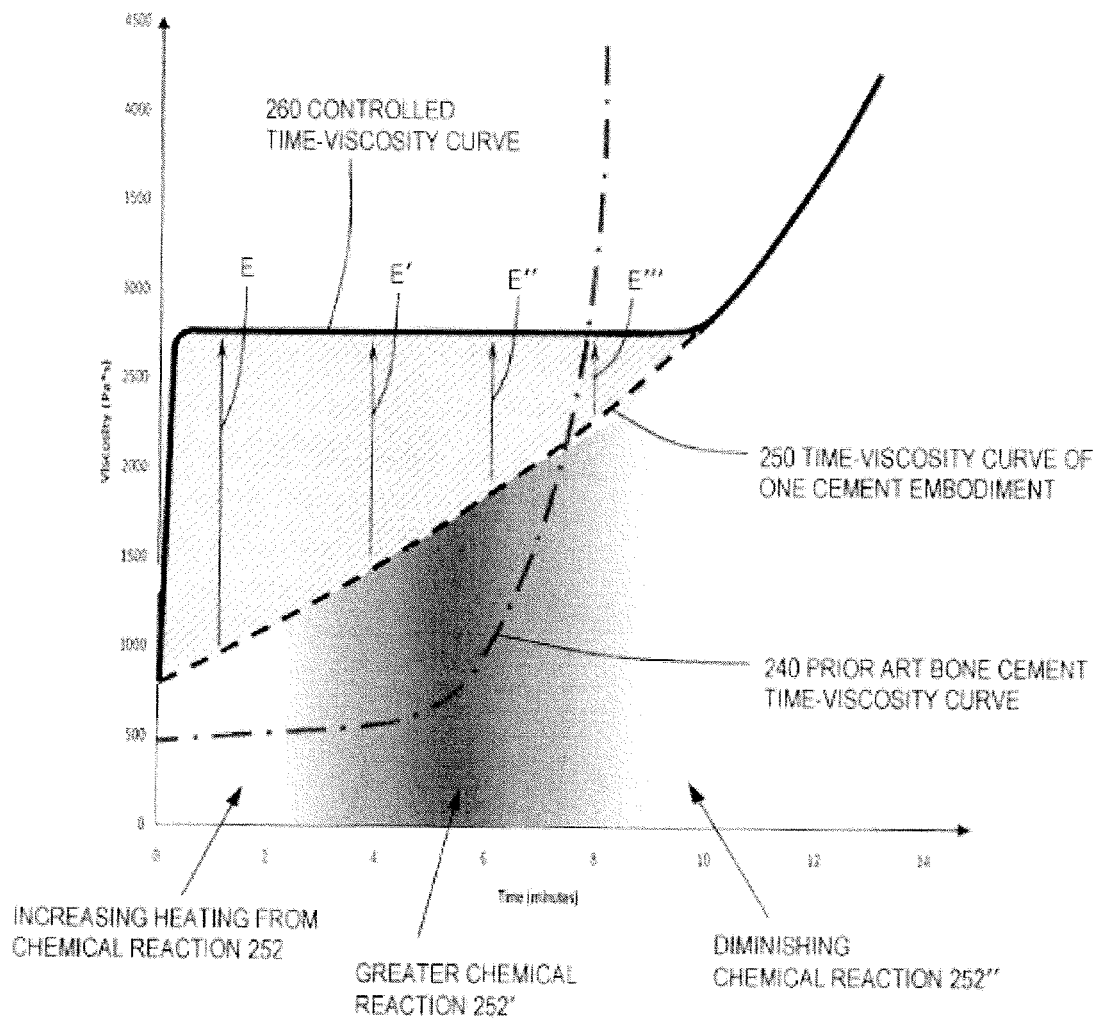
FIG. 8B is chart indicating a modified time-viscosity curve for the PMMA bone cement of FIG. 8A when modified by energy applied from an embodiment of a thermal energy emitter and a selected energy-delivery algorithm according to the present disclosure.

Now turning to FIGS. 7, 8A, and 8B, charts are presented that illustrate certain aspects of embodiments of methods for controlled application of energy to a bone cement 130 provide a cement with a controlled, on-demand increased viscosity and a controlled set time, as compared to a prior art bone cement. FIG. 7 depicts a prior art bone cement known in the art, such as a PMMA bone cement, that has a time-viscosity curve 240 where the cement substantially hardens or cures within about 8 to 10 minutes, post-mixing. On the horizontal axis of FIGS. 7, 8A, and 8B, the time point zero indicates the time at which the mixing of bone cement precursors (typically the monomer and polymer components) is substantially completed. As can be seen in the prior art bone cement of FIG. 7, the cement increases in viscosity from about 500 Pa·s to about 750 Pa·s from time zero to about 6 minutes, post-mixing. Thereafter, the cement viscosity increases very rapidly over the time interval from about 6 minutes to 8 minutes post-mixing to a viscosity greater than 4000 Pa·s. A prior art bone cement having the time-viscosity curve of FIG. 7 may be considered to have a fairly high viscosity for injection in the range of about 500 Pa·s. At this viscosity range, however, the bone cement can still possess flow characteristics that result in extravasation.

Still referring to FIG. 7, it can be further understood that the "curing reaction", also referred to herein as a cement curing source is an exothermic chemical reaction that initiates a pre-determined polymerization process that is primarily dictated by the composition and concentration of the bone cement precursors, such as the PMMA polymer, monomer, and initiator. FIG. 7 indicates the exothermic curing reaction over time as a gradation where the lighter gradation region indicates a relatively lower degree of chemical reaction and heat and the darker gradation region indicates a relatively higher degree of chemical reaction and heat leading to more rapid polymerization of the bone cement precursors.

Now turning to FIG. 8A, the time-viscosity curve 250 of one embodiment of a bone cement is shown, where the initial viscosity of the bone cement is in the range of about 750 Pa·s at approximately time zero post-mixing. Subsequently, the viscosity increases in a more linear manner over about 10 to 14 minutes post-mixing than is observed in prior art bone cements. This embodiment of bone cement can be a PMMA cement composition that provides a time-viscosity curve as in FIG. 8A, and is more particularly described in U.S. Provisional Application No. 60/899,487 filed on Feb. 5, 2007, titled Bone Treatment Systems and Methods, and U.S. patent application Ser. No. 12/024,969 filed Feb. 1, 2008, titled Bone Treatment Systems and Methods, each of which is incorporated herein by this reference in their entirety and should be considered a part of this specification.

As can be seen in FIG. 8A, the bone cement 130, or more particularly, the mixture of cement precursors, includes a first cement curing source for curing the bone cement that yields a predetermined curing response post-mixing that is indicated by the gradations of reaction under the time-viscosity curve 250. In certain embodiments, the first cement curing source may include the exothermic curing reaction described above. FIG. 8A illustrates an embodiment of the curing response obtained from the chemical curing reaction graphically, with gradation region 252 being the initiation of the chemical reaction, gradation region 252' being the peak of the chemical reaction and gradation region 252" being a diminishing portion of the chemical reaction with the corresponding increase in viscosity indicated on the vertical axis.

Now turning to FIG. 8B, another chart illustrates the same PMMA bone cement of FIG. 8A with time-viscosity curve 250 together with a modified time-viscosity curve 260 that is provided by a second cement curing source. In an embodiment, the second cement curing source can include energy applied to the bone cement 130 according to embodiments of system 100 disclosed herein, as depicted in FIGS. 1 and 4-6, which modifies the time viscosity curve 250 to yield modified time-viscosity curve 260.

Thus, FIG. 8B illustrates one embodiment of the disclosure where the first curing reaction of the bone cement (i.e., the time-viscosity curve 250) is combined with the second curing reaction contributed by the applied energy from energy source 140, controller 145, and emitter 110 to provide the "modified" or "controlled" time-viscosity curve 260 for cement injection into a bone for preventing extravasation. As can be understood from FIG. 8B, the modulation of applied energy over time from the second curing source or emitter 110, indicated schematically at energy applications E, E', E", and E'", can be provided to complement the varied energy from the first curing source (exothermic reaction) to provide a substantially constant cement viscosity over a selected working time.

This aspect of the invention allows, for the first time, a controlled and substantially constant viscosity cement at a selected viscosity level that is selected to inhibit (e.g., prevent) extravasation. This aspect of the inventive bone cement 130 and system 10 is advantageous in that a typical treatment of a vertebral compression fracture requires cement injection over a period of several minutes, for example from about 2 to 10 minutes, about 2 to 6 minutes, or about 2 to 4 minutes. The physician typically injects a small amount of bone cement, for example about 1 or 2 cc's, then pauses cement injection in order to image the injected cement to check for extravasation, then repeats the additional cement injection and imaging operations as necessary. For example, in a non-limiting embodiment, the injection and imaging operations may be repeated from about 2 to 10 times or more, where the complete treatment interval can take about 4 to 6 minutes or more. It can be easily understood that a cement with a working time of at least about 5-6 minutes is needed for a typical treatment of a VCF, otherwise the first batch of cement would be too advanced in the curing process (see FIG. 7) and a second batch of cement would need to be mixed. In the cement 130 and system 10 indicated in FIG. 8B, the cement viscosity can be approximately constant, thus providing a very long working time of about 8-10 minutes. It should be appreciated that, in the chart of FIG. 8B, the first and second curing reactions and applied energy are indicated by shaded areas below curves 250 and 260. This graphic representation is for conceptual purposes only, as the vertical axis measures viscosity in Pa·s. The actual applied energy indicated at E to E''' is determined by analysis of the actual polymerization reaction time of a selected bone cement composition at selected operating parameters that may include, but are not limited to, ambient temperature, bone cement storage temperature, bone cement temperature during and/or after mixing, atmospheric pressure, and controller motor drive pressure (e.g. pressure measured by sensor 290). Viscosity-time profile 260 may be advantageous under circumstances where injecting a bone cement having a generally uniform stiffness throughout the volume of the injected bone cement is desired.

With continued reference to FIG. 8B, the system and method provide a controller 145 and energy emitter 110 that can apply energy sufficient to very rapidly increase the viscosity of bone cement to a selected viscosity that will not allow for extravasation. As can be seen in FIG. 8B, the time-viscosity curve 260 within about 15-30 seconds can be elevated to above about 2000 Pa·s. The method of bone cement treatment encompasses utilizing an energy emitter 110 that applies energy to bone cement to controllably increase its viscosity in less than about 2 minutes or less than about 1 minute by at least 200 Pa·s, at least 500 Pa·s or at least 1,000 Pa·s. Alternatively, the method of bone cement treatment encompasses utilizing an energy emitter that applies energy to bone cement to controllably increase the viscosity in less than 2 minutes or less than 1 minute to at least 1,000 Pa·s, at least 1,500 Pa·s, at least 2,000 Pa·s, at least 2,500 Pa·s, at least 4,000 Pa·s, or at least about 5,000 Pa·s.

Thus, in one embodiment of the present disclosure, the bone cement system includes: first and second sources for causing a controlled curing reaction in a bone cement, where the first source includes a predetermined exothermic curing reaction in response to mixing cement precursor compositions and the second source includes a thermal energy emitter 110 for providing a variable curing reaction in the cement, and a controller 145 for modulating applied energy from the thermal energy emitter 110 to thereby control the curing reaction over a selected working time.

It can be understood from co-pending U.S. Provisional Application No. 60/899,487 filed on Feb. 5, 2007, titled Bone Treatment Systems and Methods and U.S. patent application Ser. No. 12/024,969 filed Feb. 1, 2008, titled Bone Treatment Systems and Methods, that PMMA cement compositions can be created to provide highly-extended working times. Such bone cements in combination with the system 10 of embodiments of the present disclosure thus allow for selected working times of at least 6 minutes, 8 minutes, 10 minutes, 12 minutes, 14 minutes, 16 minutes, 18 minutes, 20 minutes, 25 minutes. Further embodiments provide a control system that allows for providing a bone cement within a selected cement viscosity range as it exits the injector outlet 122 over the selected working time. Further embodiments provide a controller that is capable of providing a substantially constant cement viscosity over the selected working time. Additional embodiments provide a controller that is capable of providing a plurality of selected time-viscosity profiles of the cement as it exits the injector.

In one embodiment of the present disclosure, the bone cement system includes: first and second sources for causing a controlled curing reaction in a bone cement, where the first source includes a predetermined exothermic curing reaction in response to mixing cement precursor compositions and the second source includes thermal energy applied to the bone cement from an external source, and a control system that controls the thermal energy applied by the external source so as to provide a cement exiting the injector a selected viscosity of at least 600 Pa·s, 800 Pa·s, 1000 Pa·s, 1200 Pa·s, 1400 Pa·s, 1600 Pa·s, 1800 Pa·s, 2000 Pa·s, 2500 Pa·s, 3000 Pa·s, 4000 Pa·s, or at least 5,000 Pa·s.

In another embodiment, the present disclosure provides a method of preparing a curable bone cement for injection into a vertebra. The method includes mixing bone cement precursors such that a first non-variable curing reaction occurs between the precursors in the bone cement and applying energy to the bone cement from an external source to provide a second variable curing reaction in the bone cement, wherein applied energy from the second source is controlled by a controller to permit a combination non-variable and variable curing reaction thereby providing a selected cement viscosity. Further, the method includes varying the applied energy from the second source in response to the length of a post-mixing interval. Further, the method includes varying the applied energy from the second source in response to ambient temperature that is measured by a temperature sensor in the system. Further, the method includes varying the applied energy from the second source in response to a selected injection rate of the bone cement flow through the system. Further, the method includes varying the applied energy from the second source to provide a bone cement having an injection viscosity of at least 500 Pa·s, 1000 Pa·s, 1500 Pa·s, 2000 Pa·s, 3000 Pa·s, 4000 Pa·s or 5000 Pa·s.

In another embodiment, the present disclosure provides a method of preparing a curable bone cement for injection into a vertebra that includes mixing bone cement precursors thereby causing a first curing reaction characterizing the cement with a first time-viscosity profile, and actuating a controller to controllably apply energy to the bone cement from an external source, thereby modifying the first time-viscosity profile to a second time-viscosity profile, and injecting the cement having the second time-viscosity profile into the vertebra. In this method, the cement viscosity is at least 500 Pascals-second, 1000 Pa·s, 1500 Pa·s, 2000 Pa·s, 3000 Pa·s, 4000 Pa·s or at least 5000 Pa·s. The method includes actuating the controller to modulate applied energy in response to control signals selected from the group consisting of the length of a cement post-mixing interval, ambient temperature, cement temperature, and rate of cement injection.

As can be understood from FIG. 8B and the description above, one embodiment of the present disclosure allows for cement injection at a viscosity range of over 2500 Pa·s, which has been found to be beneficial for substantially inhibiting extravasation of the cement. In one embodiment, the bone treatment system can include a first source and a second source for causing a controlled curing reaction in a bone cement, where the first source can be a predetermined exothermic curing reaction in response to mixing cement precursor compositions where the second source can be a thermal energy emitter for providing a variable curing reaction, and a controller for modulating applied energy from the emitter to thereby control the curing reaction over a selected working time. The controller can preferably modulate applied energy to provide a selected cement viscosity over a working time of at least 2 minutes, 4 minutes, 6 minutes, 8 minutes, 10 minutes, 12 minutes, 14 minutes, 16 minutes, 18 minutes, 20 minutes, or 25 minutes.

In another embodiment, a bone treatment system can include a bone cement injector system, a thermal energy emitter for delivering energy to a flow of bone cement through the injector system and a controller including an algorithm for modulating applied energy from the emitter to a bone cement flow, wherein the algorithm is increases the applied energy from zero at a rate selected to inhibit vaporization of monomer portions of the bone cement.

In another embodiment of the present disclosure, the controller 145 allows for a physician to select a particular approximate cement viscosity by use of a selector mechanism operatively connected to the controller 145. In one embodiment, the physician can select among a plurality of substantially constant viscosities that can be delivered over the working time, for example, a first choice may include viscosities less than 1,000 Pa·s, and a second choice may include viscosities in excess of 1,500 Pa·s. It should be appreciated that the selections can range from two to six or more, with each selection being a viscosity range useful for a particular purpose.

Figure 9A:
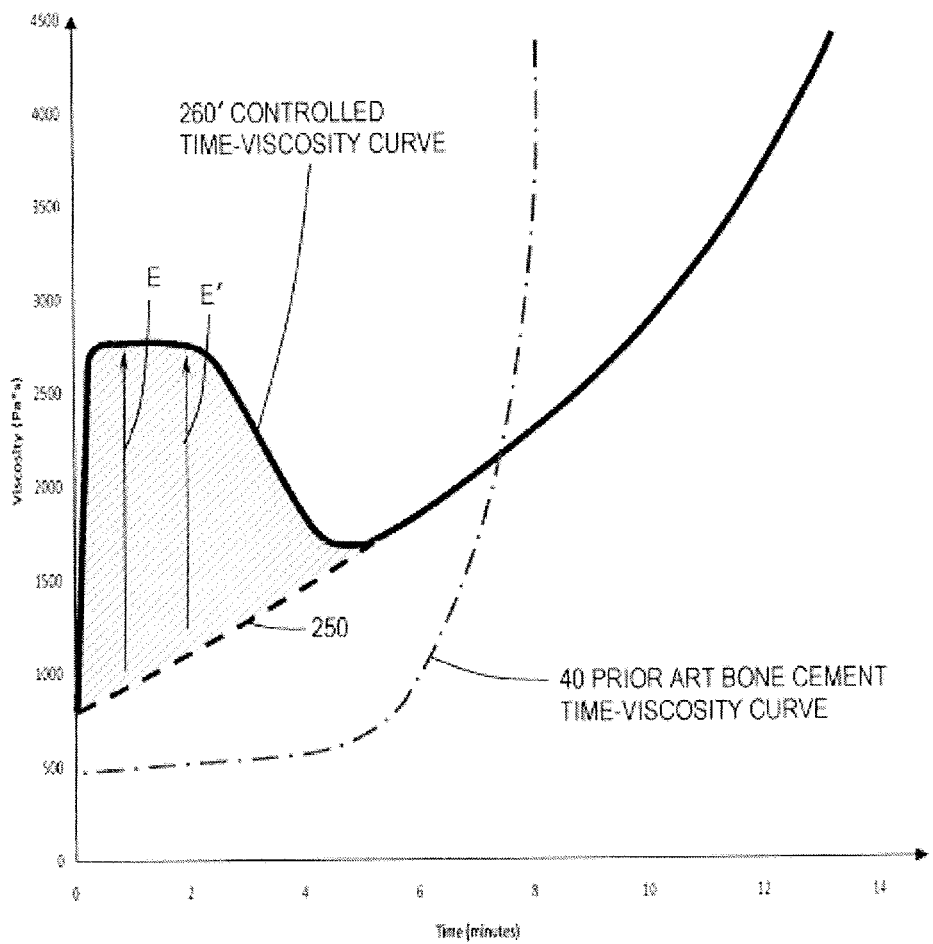
FIG. 9A is chart indicating another modified time-viscosity curve for the PMMA bone cement of FIG. 8A when modified by applied energy and an alternative energy-delivery algorithm.
Figure 9B:
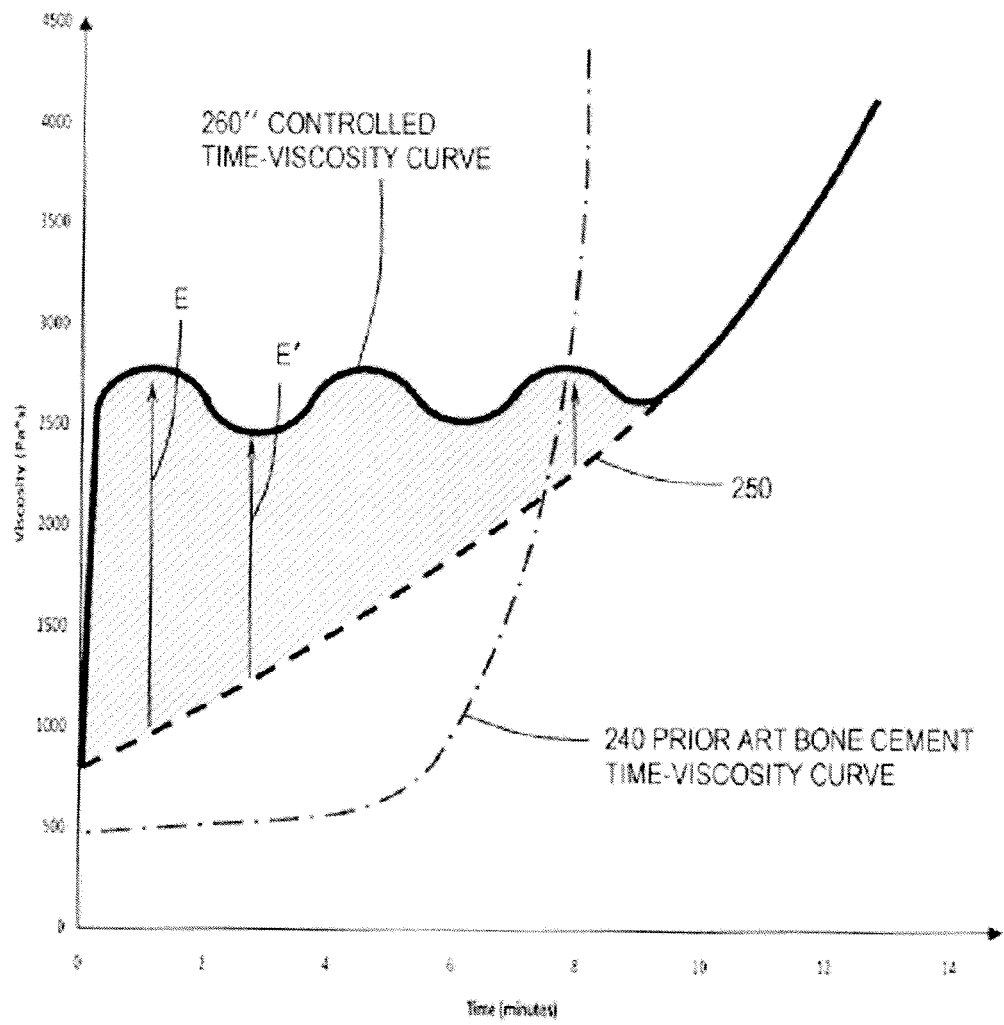
FIG. 9B is chart indicating another modified time-viscosity curve for a PMMA bone cement when modified by applied energy and an alternative energy-delivery algorithm.

In another embodiment of the present disclosure, referring to FIGS. 9A-9B, the controller may also allow the physician to select an energy-delivery algorithm in the controller 145 to provide a decrease in cement viscosity following an initial upward spike in viscosity (curve 260') following the application of energy to the cement flow (FIG. 9A). It can be seen in FIG. 9A that energy delivery by emitter indicated at E and E' is terminated, resulting in the attained viscosity in subsequent portions of the cement flow to be reduced toward the baseline viscosity of the cement 250 provided by the exothermic reaction of the bone cement precursors alone. Viscosity-time profile 260' may be advantageous under circumstances where injecting a bone cement having a relatively stiff outer surface (e.g., the portion of the bone cement having a relatively high viscosity when energy E, E' is applied) and a relatively less stiff inner core (e.g., the portion of the bone cement having viscosity reduced towards the baseline viscosity of cement 250) is desired.

Similarly, FIG. 9B indicates another energy-delivery algorithm wherein the cement flow viscosity is modulated up and down within a viscosity range indicated by time-viscosity curve 260". In certain embodiments, the viscosity of the cement flow may be modulated about a mean value of 1500 Pa·s, 2000 Pa·s, 3000 Pa·s, 4000 Pa·s and 5000 Pa·s, though other viscosity mean values are possible. In other embodiments, the amplitude of the modulated viscosity may be 50 Pa·s, 100 Pa·s, 500 Pa·s and 100 Pa·s, though other amplitude values are possible. In another embodiment, the viscosity-time profile 260" may arise under circumstances where the application of energy to the bone cement is controlled by the controller 145 in accordance with pressure measured or sensed proximate the controller motor drive 211 (e.g., via sensor 290). For example, the controller 145 may attempt to maintain a target pressure. When sensor 290 senses that the pressure exerted by the motor drive 211 increases or decreases by greater than a selected amount from the target pressure, the controller may decrease or increase, respectively, the applied energy (e.g., energy applied by the thermal energy emitter 110 to bone cement 130) in order to cause the pressure to move back towards the target pressure. Because such a control system is feedback driven, the viscosity-time profile will tend to exhibit oscillations about the target pressure.

Figure 10:
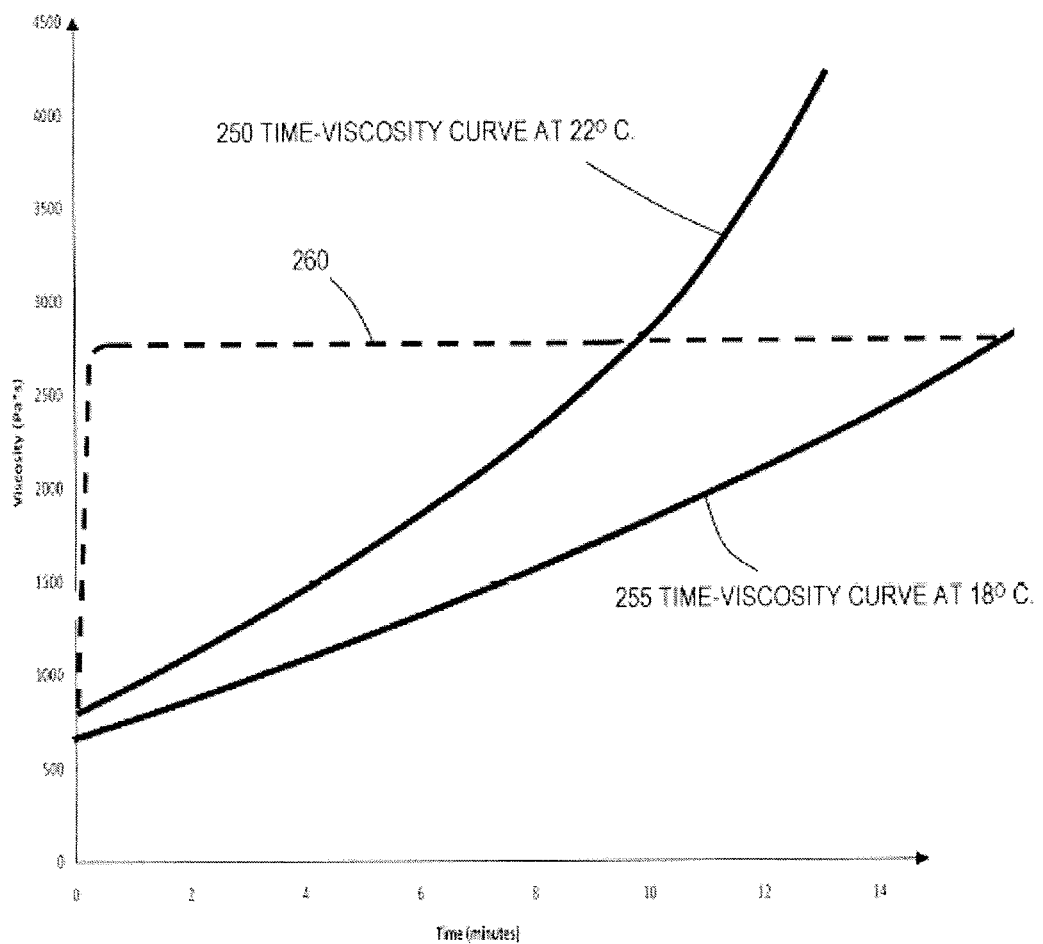
FIG. 10 is chart indicating time-viscosity curves for an embodiment of the PMMA bone cement as in FIG. 8A at different ambient temperatures.

FIG. 10 provides a schematic graphical representation of the bone cement of FIG. 8A that, after mixing exhibits the time-viscosity curves 250 and 255 corresponding to respective ambient temperatures of 22° C. and 18° C. It can be seen that different levels of applied energy would be required to achieve a similar time-viscosity curve 260 of FIG. 10. Thus, in an embodiment of a treatment method of the present disclosure, inputs may be provided to control algorithms for controlling applied energy to cement flows that factor in ambient temperatures.

Figure 11:
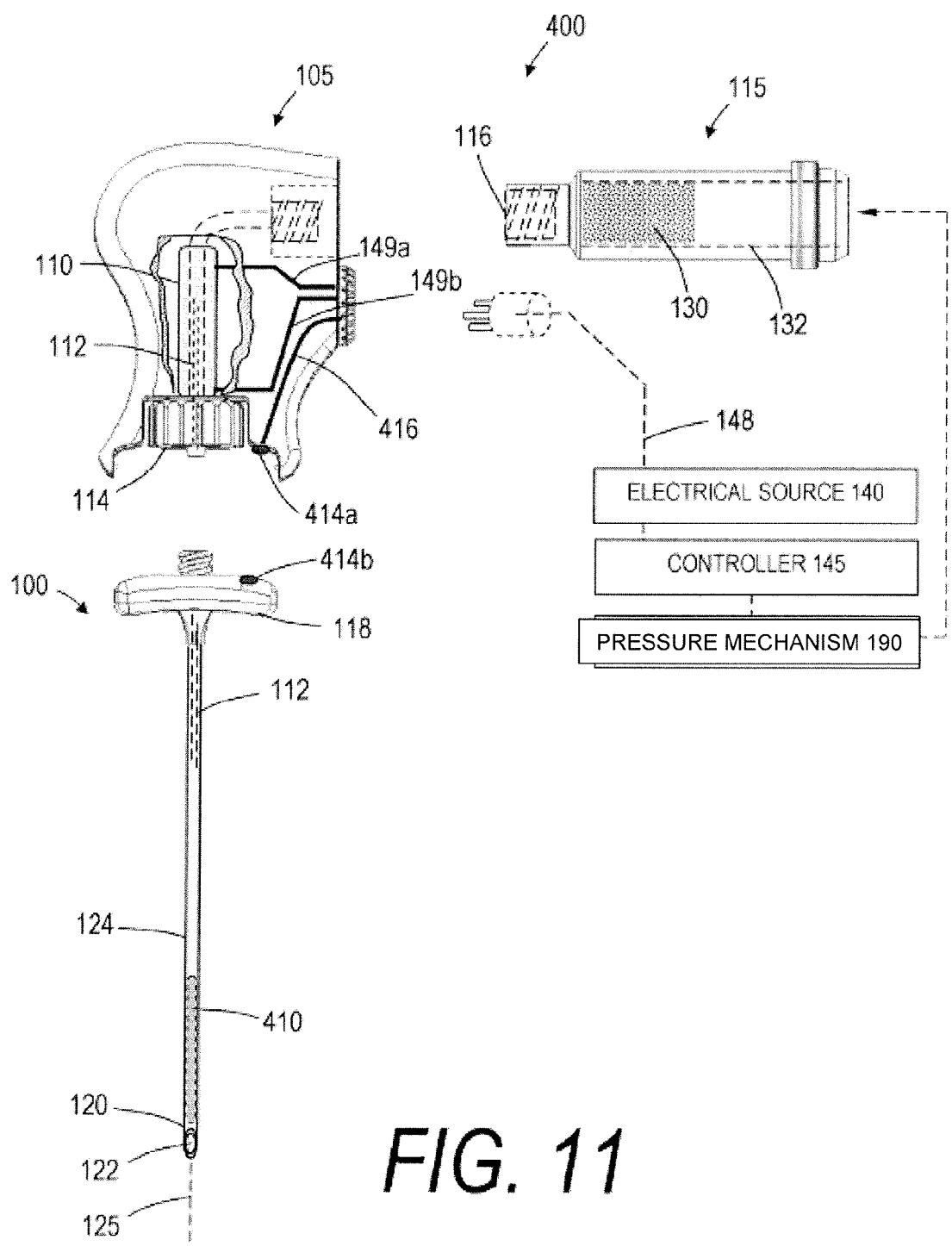
FIG. 11 is a view of another embodiment of a bone cement injection system with components de-mated from one another, where the system includes first and second thermal energy emitters.

In another embodiment, referring to FIG. 11, the bone cement system 400 includes first and second thermal energy emitters 110 and 410 for controlled application of energy to a bone cement flow within the flow passageway 112 of the injector system. More particularly, the first emitter 110 is disposed in the first handle component 105 as described previously. The second emitter 410 is disposed in a portion (e.g., medial or distal) of the second extension component 110 of the system. The controller 145 can modulate applied energy from one or both of the first and second emitters 110 and 410 to provide a controlled curing reaction of the flow of bone cement 130. In one method of use, the first emitter 110 can apply energy to heat the flow of the bone cement carried to the location of the second emitter 410 at a viscosity of less than about 500 to 1000 Pa·s. This first bone cement heating can enable the viscosity of the bone cement within the flow channel 112 to be kept within a range that can be pushed through the bone cement injector 100 with a low level of pressure. For example, the bone cement may be pushed through the injector 100 at pressures ranging between about 100 psi and about 1500 psi. Thereafter, the second emitter 410 can apply energy to heat the flow of cement and accelerate its rate of polymerization so as to achieve a viscosity greater than 2000 Pa·s. Furthermore, in one embodiment, the second emitter 110 may heat the bone cement such that the viscosity of bone cement exiting the outlet 122 can be at an even higher level, for example at a level capable of fracturing cancellous bone.

FIG. 11 further illustrates that electrical connector components 414a and 414b are provided in the interface between the first and second components, 105 and 110 to provide an electrical connection from electrical source 140 to the emitter 410 via electrical wires indicated at 416 in the handle portion 105 of the system. It should be appreciated that the second emitter 410 can be a PTCR emitter, as described previously, or any other type of heating element. The heating element can have any length including the entire length of the extension portion 124.

In one embodiment of the system, the bone cement 130 has a predetermined working time for polymerizing from an initial state to a selected endpoint of at least 10 minutes, 12 minutes, 14 minutes, 16 minutes, 18 minutes, 20 minutes, 25 minutes, 30 minutes and 40 minutes, as disclosed in co-pending Provisional application Ser. No. 60/899,487 filed Feb. 5, 2007 titled Bone Treatment Systems and Methods. In an embodiment, the selected endpoint may include providing the bone cement 130 in a partly polymerized condition having a viscosity within a selected viscosity range that substantially inhibits cement extravasation. In a non-limiting embodiment, extravasation may be inhibited when the bone cement viscosity is greater than about 2000 Pa·s.

The energy source 140 may accelerate a polymerization rate of the bone cement by at least 20%, 30%, 40%, 50%, 60%, 70%, 80%, 90% and 95% over that which would be achieved absent application of energy to the bone cement from the energy source. In another embodiment, the energy source 140 and controller 145 may accelerate the polymerization rate of the cement such that the selected endpoint of the bone cement is achieved in less than 1 second, 5 seconds, 10 seconds, 20 seconds, 30 seconds, 45 seconds, 60 seconds and 2 minutes.

In an embodiment of a method of using the system 10 of FIGS. 1-6, the method of treating a vertebra includes (i) introducing a cement injector needle into a vertebra, the needle having a flow channel extending from a proximal injector end to a distal injector end with a flow outlet, (ii) causing a flow of bone cement from the source through a flow channel in the an energy-delivery component and the injector needle, and (iii) applying energy from the energy-delivery component to the flow to cause the bone cement to exhibit a different setting rate to reach a selected polymerization endpoint. In this method, the applied energy accelerates setting of pre-polymerized bone cement before exiting the flow outlet. The method and the selected polymerization endpoint provide a viscosity that substantially prevents cement extravasation following introduction into the vertebra.

In another embodiment of the method, the energy-delivery emitter 110 is actuated by the operator from a location outside any imaging field.

In a further embodiment of the method, the energy-delivery emitter 110 may be actuated to apply energy of at least 0.01 Watt, 0.05 Watt, 0.10 Watt, 0.50 Watt and 1.0 Watt. In another aspect of the method, the applied energy is modulated by controller 145. In another aspect of the method, the energy source and controller may accelerate the polymerization rate of the bone cement to reach the selected endpoint in less than 1 second, 5 seconds, 10 seconds, 20 seconds, 30 seconds, 45 seconds, 60 seconds and 2 minutes. In another aspect of the method, the energy source and controller may accelerate the polymerization rate of the bone cement by at least 20%, 30%, 40%, 50%, 60%, 70%, 80%, 90% and 95%.

In another embodiment of the present disclosure, a method of bone cement injection accordingly includes modulating the rate of cement flow in response to determining a selected parameter of the cement flow such as flow rate. The method of bone cement injection further included applying and modulating thermal energy application from an emitter in the injector body to the cement flow. The method of bone cement injection further includes modulating the application of energy in response to signals that relate to a selected parameter such as flow rate of the cement flow.

Of particular interest, another embodiment of a method of bone cement injection includes (a) providing a bone cement injector body carrying a PTCR (positive temperature coefficient of resistance) material in a flow channel therein, (b) applying a selected level of energy to a cement flow through the PTCR material, and (c) utilizing an algorithm that processes impedance values of the PTCR material to determine the cement flow rate. The method of bone cement injection further includes modulating a cement injection parameter in response to the processed impedance values.

Another embodiment of a method of bone cement injection includes (a) providing a bone cement injector body carrying a PTCR material or other thermal energy emitter in a flow channel therein, (b) causing a selected cement flow rate and a selected level of energy delivery to the cement flow through the emitter, and (c) modulating the selected flow rate and/or energy delivery to maintain a substantially constant impedance value of the emitter material over a cement injection interval. The selected cement injection interval can be at least 1 minute, at least 5 minutes, at least 10 minutes and at least 15 minutes.

In another embodiment, of the method, the selected flow rate and/or energy delivery may be modulated to maintain a substantially constant viscosity of bone cement ejected from the injector over a cement injection interval. The system and energy source may apply energy of at least 0.01 Watt, 0.05 Watt, 0.10 Watt, 0.50 Watt and 1.0 Watt. In another aspect, the energy source and controller may accelerate polymerization rate of the bone cement to a selected endpoint in less than 1 second, 5 seconds, 10 seconds, 20 seconds, 30 seconds, 45 seconds, 60 seconds and 2 minutes.

Another embodiment of a method of bone cement injection utilizes systems such as system 10 and 400 as described above and include (a) providing a bone cement injector body with a flow channel extending therethrough from a proximal handle end though a medial portion to a distal end portion having a flow outlet, (b) causing cement flow through the flow channel, and (c) warming the cement flow with an energy emitter in a proximal end or medial portion thereof to initiate or accelerate polymerization of the cement of the cement flow. The method may further include providing a flow rate of the cement flow that ranges from 0.1 cc/minute to 20 cc/minute, from 0.2 cc/minute to 10 cc/minute, and from 0.5 cc/minute to 5 cc/minute.

Of particular interest, embodiments of the above-described methods of bone cement injection provide delivery of bone cement at a predetermined cement flow rate so as to allow cement flows a selected interval over which they are allowed to polymerize in the flow channel downstream from the energy emitter. This method includes providing a selected interval of greater than 1 second, greater than 5 seconds, greater than 10 seconds, greater than 20 seconds, and greater than 60 seconds.

The above-described method utilizes an energy emitter that applies energy sufficient to elevate the temperature of the bone cement by at least 1° C., at least 2° C., and at least 5° C. The method of bone cement injection includes utilizing an energy emitter that applies at least 0.1 Watt of energy to the cement flow, at least 0.5 Watt of energy to the cement flow, and at least 1.0 Watt of energy to the cement flow. The method includes the flow rate of the cement flow being adjusted in intervals by controller 145, or being continuously adjusted by a controller.

The above disclosed embodiments are intended to be illustrative and not exhaustive. Particular characteristics, features, dimensions, and the like that are presented in dependent claims can be combined and fall within the scope of the invention. The invention also encompasses embodiments as if dependent claims were alternatively written in a multiple dependent claim format with reference to other independent claims. Specific characteristics and features of the invention and its method are described in relation to some figures and not in others, and this is for convenience only. While the principles of the invention have been made clear in the embodiments described above, it will be obvious to those skilled in the art that modifications may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

Of course, the foregoing description is that of certain features, aspects and advantages of the present invention, to which various changes and modifications can be made without departing from the spirit and scope of the present invention. Moreover, the bone treatment systems and methods need not feature all of the objects, advantages, features and aspects discussed above. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of these specific features and aspects of embodiments may be made and still fall within the scope of the invention. Accordingly, it should be understood that various features and aspects of the disclosed embodiments can be combined with or substituted for one another in order to form varying modes of the discussed bone treatment systems and methods.

What is claimed is:

1. A method for treating a bone, comprising:
   inserting at least a portion of an injector of a bone cement injector system within a vertebral body;
   providing a flow of a settable bone cement into a proximal portion of the injector;
   applying a first non-zero level of energy at a first time to the bone cement via one or more thermal energy emitters of the bone cement injector system to cause the bone cement to change to a first viscosity,
   applying a second non-zero level of energy at a second time to the bone cement via the one or more thermal energy emitters to cause the bone cement to change to a second viscosity, wherein the first time is before the second time and the first non-zero level of energy is unequal to the second non-zero level of energy,
   wherein the application of the first and second non-zero levels of energy is controlled based at least in part on a sensed force applied to the bone cement injector system to modulate the viscosity of the bone cement between the first and second viscosities about a desired mean viscosity value;
   urging the bone cement from the proximal portion toward a distal portion of the injector; and
   introducing the bone cement into cancellous bone of the vertebral body.

2. The method of claim 1, wherein applying first and second non-zero levels of energy to the bone cement comprises executing at least one algorithm stored by a computer readable medium to controllably modulate the levels of energy applied by at least one of the thermal energy emitters.

3. The method of claim 2, wherein the at least one algorithm comprises a plurality of preset algorithms.

4. The method of claim 2, further comprising selecting an algorithm from a plurality of algorithms, the selected algorithm being one that causes the bone cement introduced into the cancellous bone to interdigitate with the cancellous bone.

5. The method of claim 4, wherein the first viscosity of the bone cement is at least 2000 Pa·s.

6. The method of claim 1, wherein the desired mean viscosity value is selected from the group consisting of 1500 Pa·s, 2000 Pa·s, and 3000 Pa·s.

7. The method of claim 1, wherein the first viscosity is between 2500 Pa·s and 3000 Pa·s.

8. The method of claim 1, wherein the second non-zero level of applied energy is less than the first non-zero level of applied energy.

9. The method of claim 1, further comprising delivering a third non-zero level of applied energy at a third time to cause the bone cement to change to the first viscosity.

10. The method of claim 9, further comprising delivering a fourth non-zero level of applied energy at a fourth time to cause the bone cement to change to the second viscosity.

11. A method for treating a bone, comprising:
    flowing bone fill material through a bone fill material injector system having at least a portion of an injector positioned in a cancellous bone portion of the bone;
    delivering a first non-zero level of applied energy to the flow of bone fill material via a thermal energy emitter in communication with the bone fill material injector system, wherein delivering the first non-zero level of applied energy changes the viscosity of the bone fill material to a first viscosity;
    delivering a second non-zero level of applied energy to the flow of bone fill material via the thermal energy emitter after delivering the first non-zero level of applied energy, wherein delivering the second non-zero level of applied energy changes the viscosity of the bone fill material to a second viscosity less than the first viscosity, the first and second viscosities defining a viscosity range therebetween;
    delivering a third non-zero level of applied energy to the flow of bone fill material via the thermal energy emitter after delivering the second non-zero level of applied energy, wherein delivering the third non-zero level of applied energy changes the viscosity of the bone fill material to the first viscosity;
    wherein the third non-zero level of applied energy is less than the first non-zero level of applied energy; and
    electronically controlling the delivery of the first, second, and third non-zero levels of energy via the thermal energy emitter to modulate the viscosity of the bone fill material about a desired mean bone fill material viscosity within the viscosity range based at least in part on a sensed parameter of the bone fill material injector system.

12. The method of claim 11, further comprising electronically controlling a drive pressure of the bone fill material flow through the injector system.

13. The method of claim 12, wherein electronically controlling one or both of the energy delivery and drive pressure comprises controlling one or both of energy delivery and drive pressure to achieve a mean viscosity within the viscosity range selected from the group consisting of at least 1500 Pa·s, at least 2000 Pa·s, at least 2500 Pa·s, at least 3000 Pa·s, at least 3500 Pa·s, at least 4000 Pa·s, at least 4500 Pa·s, at least 5000 Pa·s, and greater than 5000 Pa·s.

14. The method of claim 11, wherein the second non-zero level of applied energy is less than the first non-zero level of applied energy.

15. The method of claim 11, wherein desired mean bone fill material viscosity is selected from the group consisting of 1500 Pa·s, 2000 Pa·s, and 3000 Pa·s.

16. The method of claim 11, wherein an amplitude of the modulated viscosity is selected from the group consisting of 50 Pa·s, 100 Pa·s, and 500 Pa·s.

17. The method of claim 11, wherein the first viscosity is between 2500 Pa·s and 3000 Pa·s.

18. The method of claim 11, wherein the first viscosity of the bone cement is at least 2000 Pa·s.

19. The method of claim 11, wherein applying first, second, and third non-zero levels of energy comprises executing at least one algorithm stored by a computer readable medium to controllably modulate the levels of energy applied by at least one of the thermal energy emitters.

20. The method of claim 19, wherein the at least one algorithm comprises a plurality of preset algorithms.

* * * * *